(12) United States Patent
Cicenas et al.

(10) Patent No.: US 7,465,278 B2
(45) Date of Patent: Dec. 16, 2008

(54) DEVICE FOR MINIMALLY INVASIVE INTERNAL TISSUE REMOVAL

(75) Inventors: Chris W. Cicenas, Columbus, OH (US); Jeffrey W. Servaites, Columbus, OH (US); Andrew T. Beckman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 176 days.

(21) Appl. No.: 11/392,147

(22) Filed: Mar. 29, 2006

(65) Prior Publication Data

US 2007/0239064 A1    Oct. 11, 2007

(51) Int. Cl.
A61B 10/00 (2006.01)

(52) U.S. Cl. ..................................... 600/565
(58) Field of Classification Search ......... 600/562–568; 606/167, 170, 184, 185; 604/159, 239, 264, 604/272, 506, 512
See application file for complete search history.

(56) References Cited

U.S. PATENT DOCUMENTS

| | | | |
|---|---|---|---|
| 1,867,624 A | 7/1932 | Hoffman | |
| 2,716,035 A | 8/1955 | Thorndike | |
| 3,003,235 A | 10/1961 | Temple et al. | |
| 3,328,876 A | 7/1967 | Hoppe | |
| 3,364,572 A | 1/1968 | Hoppe | |
| 3,372,477 A | 3/1968 | Hoppe | |
| 3,606,878 A | 9/1971 | Kellogg, Jr. | |
| 3,800,783 A | 4/1974 | Jamshidi | |
| 3,802,074 A | 4/1974 | Hoppe | |
| 3,815,604 A | 6/1974 | O'Malley et al. | |
| 3,877,434 A | 4/1975 | Ferguson et al. | |
| 3,929,123 A | 12/1975 | Jamshidi | |
| 3,995,619 A | 12/1976 | Glatzer | |
| 4,011,869 A | 3/1977 | Seiler, Jr. | |
| 4,099,529 A | 7/1978 | Peyman | |
| 4,111,207 A | 9/1978 | Seiler, Jr. | |
| 4,210,146 A | 7/1980 | Banko | |

(Continued)

FOREIGN PATENT DOCUMENTS

DE           86 23 592        10/1987

(Continued)

OTHER PUBLICATIONS

EPO Search Report for Application No. 07251325.2, dated Aug. 16, 2007.

*Primary Examiner*—Max Hindenburg
*Assistant Examiner*—Brian Szmal
(74) *Attorney, Agent, or Firm*—Frost Brown Todd LLC (57) ABSTRACT

A medical device for severing and removing small amounts of internal tissue for biopsy sampling or other purposes is disclosed. Versions of the device may include a hollow probe having a tissue receiving aperture; a cutter having a cutting edge that moves past the tissue receiving aperture, and a cutter driving mechanism. Versions of the device also may include a vacuum plunger within the probe, and coordinated actuation of the vacuum plunger and the cutter driving mechanism whereby an effective vacuum is developed and maintained within the probe to draw tissue into the tissue receiving aperture prior to and during a cutting stroke of the cutter. Versions described may be used for removing multiple samples of tissue during a single insertion of the probe proximate to a target tissue mass.

19 Claims, 11 Drawing Sheets

U.S. PATENT DOCUMENTS

| | | | |
|---|---|---|---|
| 4,577,629 A | 3/1986 | Martinez |
| 4,698,710 A | 10/1987 | Suganuma |
| 4,753,234 A | 6/1988 | Martinez |
| 4,819,635 A | 4/1989 | Shapiro |
| 4,900,300 A | 2/1990 | Lee |
| 4,961,430 A | 10/1990 | Sheahon |
| 5,015,250 A | 5/1991 | Foster |
| 5,060,658 A | 10/1991 | Dejter, Jr. et al. |
| 5,084,058 A | 1/1992 | Li |
| 5,087,263 A | 2/1992 | Li |
| 5,106,364 A | 4/1992 | Hayafuji et al. |
| 5,133,723 A | 7/1992 | Li et al. |
| 5,163,946 A | 11/1992 | Li |
| 5,312,422 A | 5/1994 | Trott |
| 5,324,298 A | 6/1994 | Phillips et al. |
| 5,405,354 A | 4/1995 | Sarrett |
| 5,439,467 A | 8/1995 | Benderev et al. |
| 5,469,860 A | 11/1995 | De Santis |
| 5,474,565 A | 12/1995 | Trott |
| 5,511,556 A | 4/1996 | DeSantis |
| 5,526,822 A | 6/1996 | Burbank et al. |
| 5,536,273 A | 7/1996 | Lehrer |
| 5,560,373 A | 10/1996 | De Santis |
| 5,591,177 A | 1/1997 | Lehrer |
| 5,609,597 A | 3/1997 | Lehrer |
| 5,649,547 A | 7/1997 | Ritchart et al. |
| 5,720,760 A | 2/1998 | Becker et al. |
| 5,769,086 A | 6/1998 | Ritchart et al. |
| 5,775,333 A | 7/1998 | Burbank et al. |
| 5,788,651 A | 8/1998 | Weilandt |
| 5,817,033 A | 10/1998 | DeSantis et al. |
| 5,890,309 A | 4/1999 | Markarian |
| 5,928,164 A | 7/1999 | Burbank et al. |
| 5,964,716 A | 10/1999 | Gregoire et al. |
| 5,971,939 A | 10/1999 | DeSantis et al. |
| 5,980,469 A | 11/1999 | Burbank et al. |
| 6,007,497 A | 12/1999 | Huitema |
| 6,017,316 A | 1/2000 | Ritchart et al. |
| 6,027,514 A | 2/2000 | Stine et al. |
| 6,077,230 A | 6/2000 | Gregoire et al. |
| 6,086,544 A | 7/2000 | Hibner et al. |
| 6,120,462 A | 9/2000 | Hibner et al. |
| 6,143,006 A | 11/2000 | Chan |
| 6,228,055 B1 | 5/2001 | Foerster et al. |
| 6,231,522 B1 | 5/2001 | Voegele et al. |
| 6,273,862 B1 | 8/2001 | Privitera et al. |
| 6,280,447 B1 | 8/2001 | Marino et al. |
| 6,471,659 B2 | 10/2002 | Eggers et al. |
| 6,471,700 B1 | 10/2002 | Burbank et al. |
| 6,494,844 B1 | 12/2002 | Van Bladel et al. |
| 6,517,498 B1 | 2/2003 | Burbank et al. |
| 6,540,694 B1 | 4/2003 | Van Bladel et al. |
| 6,540,695 B1 | 4/2003 | Burbank et al. |
| 6,551,255 B2 | 4/2003 | Van Bladel et al. |
| 6,554,779 B2 | 4/2003 | Viola et al. |
| 6,557,196 B2 | 5/2003 | Falbo, Sr. et al. |
| 6,585,664 B2 | 7/2003 | Burdorff et al. |
| 6,592,610 B2 | 7/2003 | Beyar |
| 6,602,204 B2 | 8/2003 | Dubrul et al. |
| 6,610,020 B2 | 8/2003 | Voegele |
| 6,620,111 B2 | 9/2003 | Stephens et al. |
| 6,626,849 B2 | 9/2003 | Huitema et al. |
| 6,626,903 B2 | 9/2003 | McGuckin, Jr. et al. |
| 6,629,986 B1 | 10/2003 | Ross et al. |
| 6,656,133 B2 | 12/2003 | Voegele et al. |
| 6,689,072 B2 | 2/2004 | Kaplan et al. |
| 6,695,852 B2 | 2/2004 | Gleason |
| 6,699,206 B2 | 3/2004 | Burbank et al. |
| 6,709,408 B2 | 3/2004 | Fisher |
| 6,712,773 B1 | 3/2004 | Viola |
| 6,712,775 B2 | 3/2004 | Burbank et al. |
| 6,714,808 B2 | 3/2004 | Klimberg et al. |
| 6,716,224 B2 | 4/2004 | Singhatat |
| 6,730,044 B2 | 5/2004 | Stephens et al. |
| 6,730,045 B2 | 5/2004 | Finer |
| 6,733,509 B2 | 5/2004 | Nobles et al. |
| 6,752,768 B2 | 6/2004 | Burdorff et al. |
| 6,852,108 B2 | 2/2005 | Barry et al. |
| 6,860,860 B2 | 3/2005 | Viola |
| 6,872,185 B2 | 3/2005 | Fisher |
| 6,908,440 B2 | 6/2005 | Fisher |
| 6,922,380 B2 | 7/2005 | Kadlec et al. |
| 6,942,627 B2 | 9/2005 | Huitema |
| 6,945,942 B2 | 9/2005 | Van Bladel et al. |
| 7,022,085 B2 * | 4/2006 | Cooke et al. ................. 600/564 |
| 7,278,970 B2 * | 10/2007 | Goldenberg ................. 600/564 |
| 2001/0041901 A1 | 11/2001 | Furusawa |
| 2001/0053916 A1 | 12/2001 | Rioux |
| 2002/0049458 A1 | 4/2002 | Singhalat |
| 2002/0050277 A1 | 5/2002 | Beyer |
| 2002/0087178 A1 | 7/2002 | Nobles et al. |
| 2003/0139752 A1 | 7/2003 | Pasrcha et al. |
| 2003/0199753 A1 | 10/2003 | Hibner et al. |
| 2004/0068231 A1 | 4/2004 | Blondeau |
| 2004/0153003 A1 | 8/2004 | Cicenas et al. |
| 2005/0203440 A1 * | 9/2005 | Gellman et al. ............. 600/567 |

FOREIGN PATENT DOCUMENTS

| | | |
|---|---|---|
| EP | 1 428 477 | 6/2004 |
| RU | 1225547 | 4/1986 |
| RU | 001834651 | 8/1993 |

* cited by examiner

FIG. 18

DEVICE FOR MINIMALLY INVASIVE INTERNAL TISSUE REMOVAL

BACKGROUND

Devices utilizing hollow probe aspiration are useful for removing and/or obtaining samples of tissue in minimally invasive percutaneous procedures, for biopsy or other purposes. Numerous potential applications exist for such devices.

It may be desirable to provide additional and alternative designs for an instrument including a hollow probe that allows for effective and efficient sample cutting and removal, minimal trauma to tissue and to the patient in the tissue removal procedure, and relatively simple design and manufacture.

A variety of biopsy devices have been developed and used, but to the best of the inventors' knowledge, no one prior to the inventors has created or used the invention described in the appended claims.

BRIEF DESCRIPTION OF THE DRAWINGS

While the specification concludes with claims that particularly point out and distinctly claim the invention, it is believed the present invention will be better understood from the following description taken in conjunction with the accompanying drawings, in which like reference numerals identify the same elements. The drawings and detailed description which follow are intended to be merely illustrative and are not intended to limit the scope of the invention as set forth in the appended claims. In the drawings:

DETAILED DESCRIPTION OF EMBODIMENTS OF THE INVENTION

Versions of a device described and illustrated herein are directed to an efficient system and method for removing tissue in a minimally invasive procedure for biopsy sampling or other purposes. In particular, versions described herein are directed to a device having a hollow probe with a receiving aperture, and a cutter within the probe having a cutting edge, for efficiently drawing in, cutting and removing tissue in a percutaneous procedure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

For purposes of the description contained herein, with respect to components described herein, the term "integral" refers to two or more identifiable components that are either formed as a single unit or, alternatively, are otherwise joined or attached together such that they move and/or operate substantially as a single unit. The term "integral" is not intended to be limited to identifiable components that are continuous or formed from a homogeneous continuum of material. However, it should be understood that the identification of separately identifiable components joined together so as to operate substantially integrally is not meant to imply that separately identifiable components are necessarily required, and is not intended to limit the scope of the claims.

For purposes of the description contained herein, "vacuum" means pressure within a space that is lower by any amount than atmospheric or ambient pressure, and although not exclusive of a condition of absolute vacuum defined by a complete absence within a space of air, fluid or other matter, the term as used herein is not meant to require or be limited to such a condition.

Figure 1:
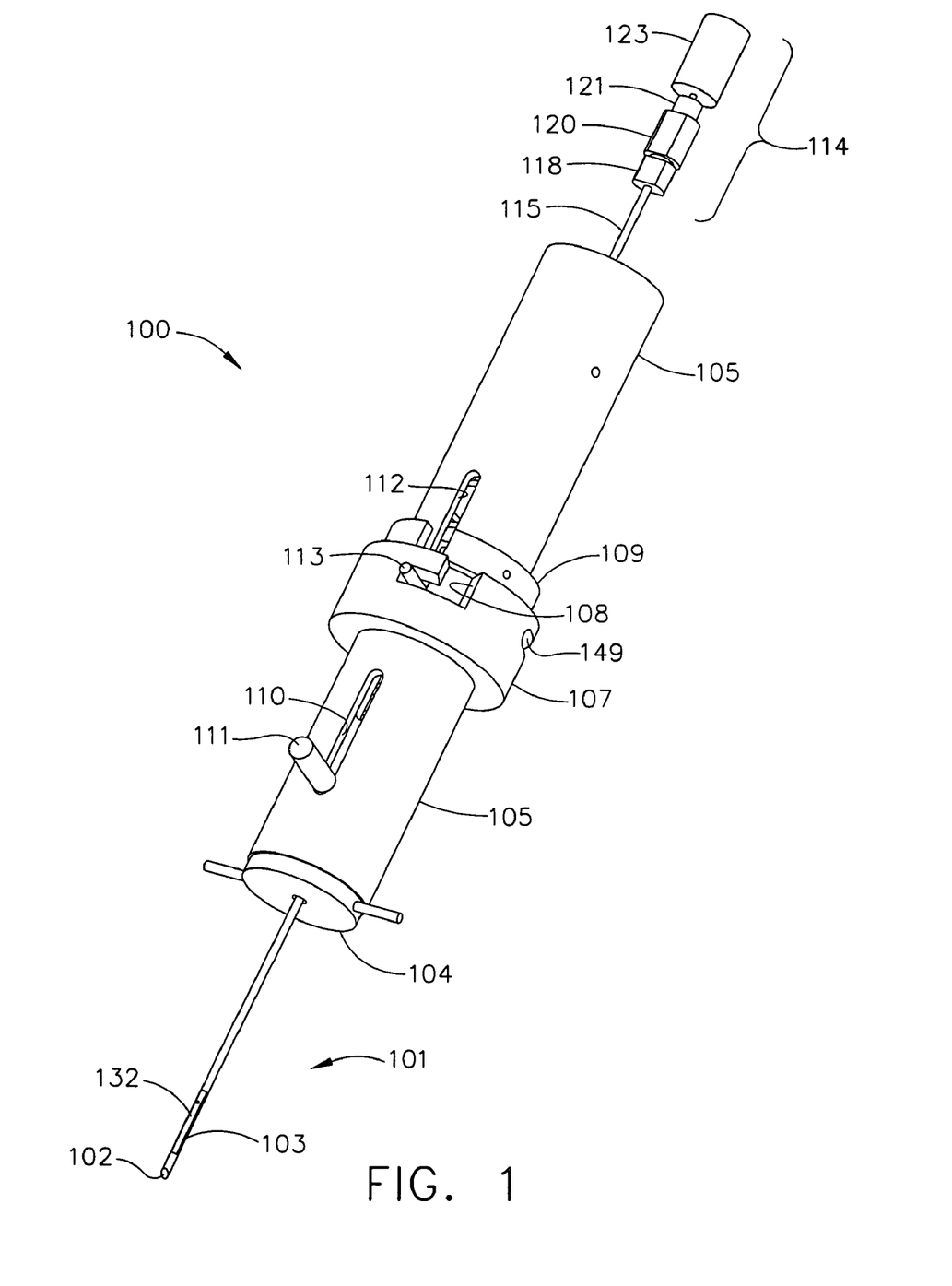
FIG. 1 is a perspective view of an exemplary version of a device for severing internal tissues and removing the severed tissues, shown in a pre-deployment position.
Figure 3:
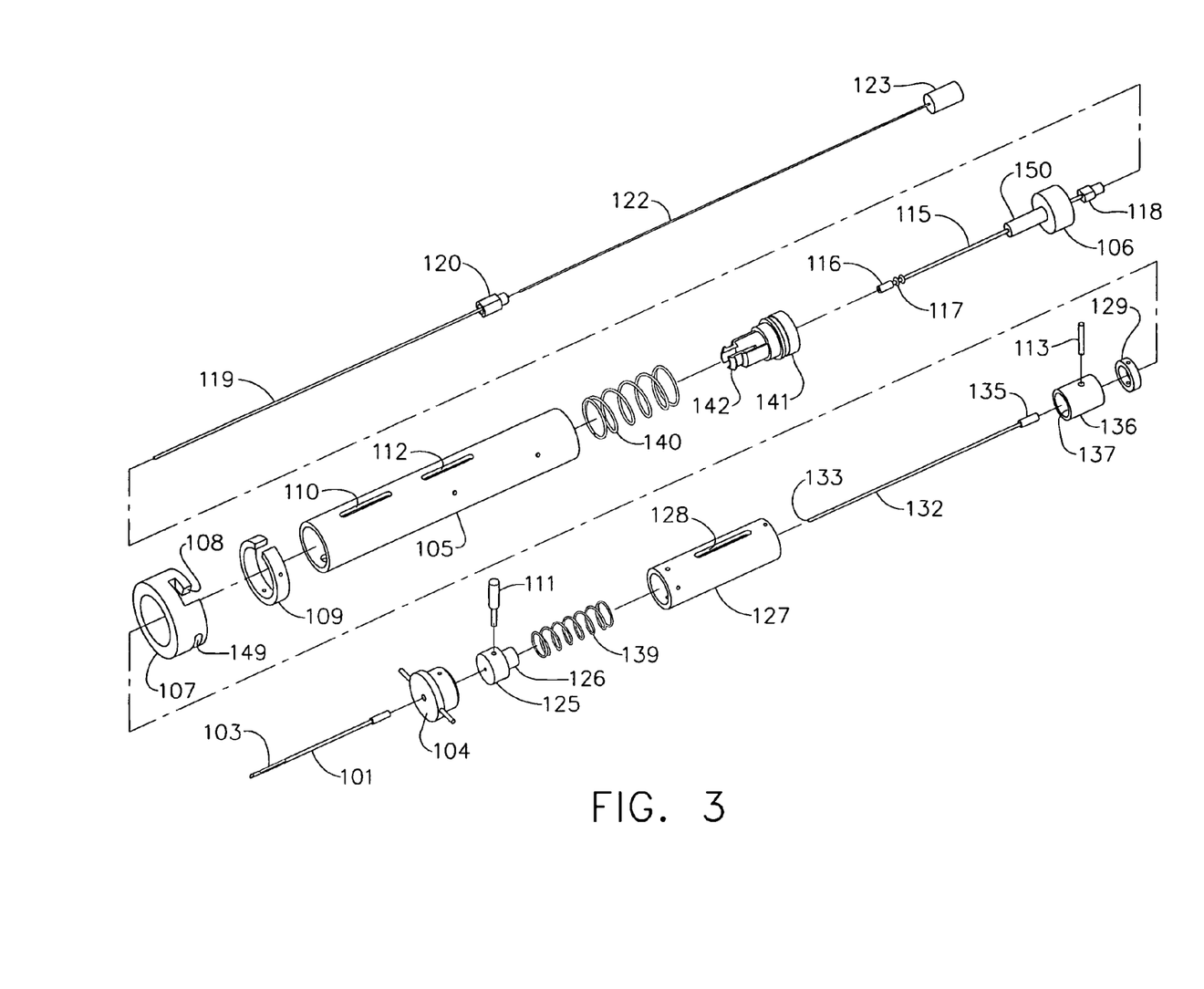
FIG. 3 is a perspective exploded view of the device shown in FIG. 1, showing its components.

Referring now to the drawings, FIGS. 1 and 3 depict one possible example of a device for severing internal tissues and removing the severed tissues. Device 100 includes probe 101 having piercing tip 102 and receiving aperture 103. In FIG. 1, the distal portion of a cutter 132 is visible in receiving aperture 103. Probe 101 is integrally affixed within forward stop 104 by set screws or any other suitable method, and forward stop 104 is in turn integrally affixed within body 105 by screws or any other suitable method. Body 105 has shoulder ring 109 mounted thereon by any suitable method. Shoulder ring 109 axially supports cutter latch ring 107, which may be rotated on body 105 within the limits created by rotation slot 149 and a rotation limiting pin (not shown) which interacts therewith, integral with body 105. Cutter latch ring 107 also has cutter latch 108 formed therein.

Figure 4:
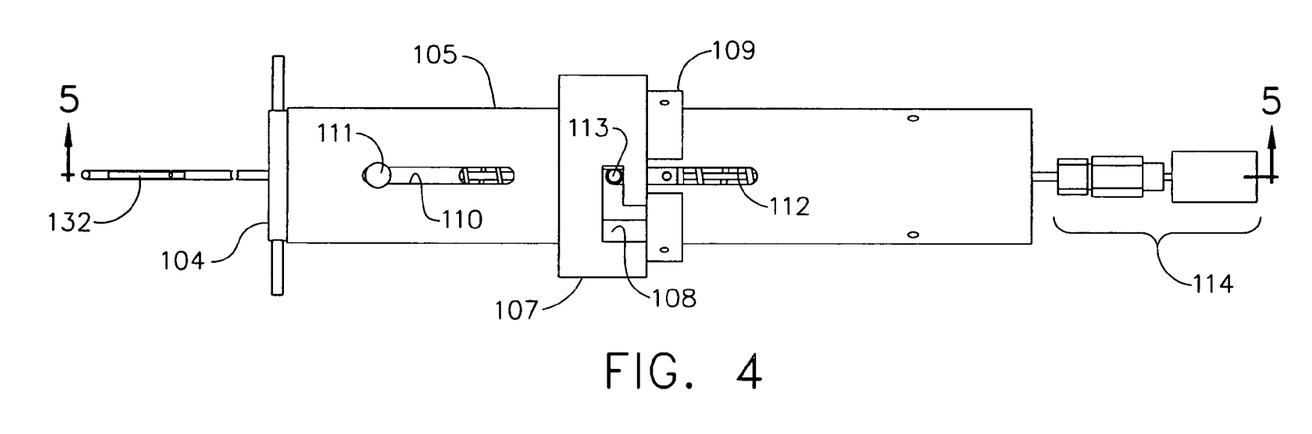
FIG. 4 is a side view of the device in FIG. 1, in its pre-deployment position.
Figure 5:
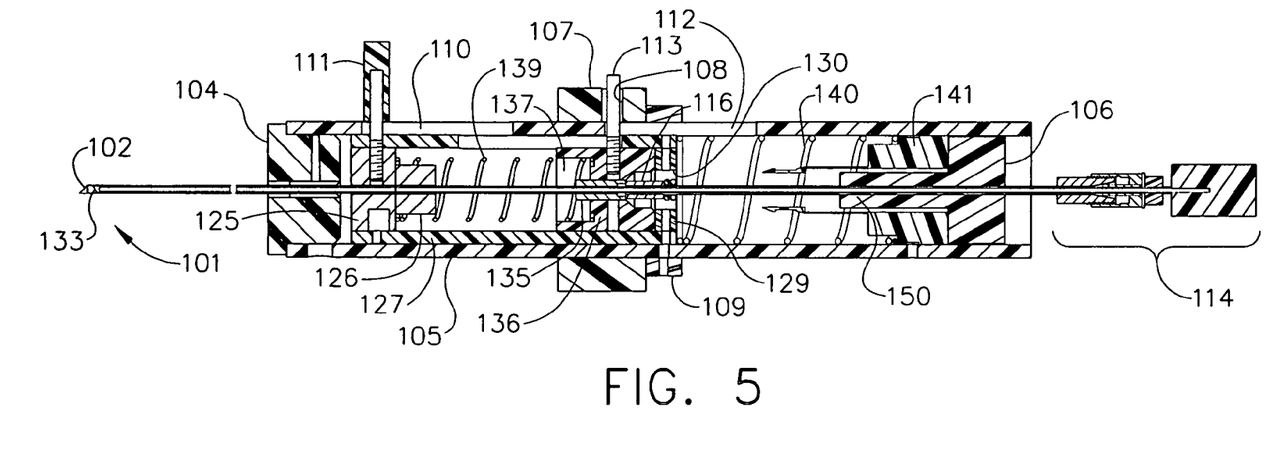
FIG. 5 is a longitudinal cross-sectional view of the device as shown in FIG. 4.

Referring to FIGS. 1, 4 and 5, which depict the exemplary version described in its pre-deployment position, and also the exploded view in FIG. 3, probe 101 is hollow, and tubular cutter 132, collection tube 119, and plunger rod 122, respectively, are situated coaxially therewithin. When the device is in its pre-deployment position, the distal ends of collection tube 119 and plunger rod 122 are substantially proximate to the cutting tip 133 of cutter 132. Cutting tip 133 has a cutting edge formed and sharpened thereon. Cutter 132 has integral cutter end collar 135 thereon, and cutter end collar 135 is integrally affixed by one or more set screws or any other suitable method within cutter block 136. Cutter latch pin 113 is integrally affixed to cutter block 136 by any suitable method, and as can be appreciated from the drawings, is permitted to move longitudinally along outer firing slot 112 in body 105 when released.

In the example depicted, cutter block 136 resides within vacuum spring tube 127, and may move longitudinally therewithin, to a rearwardmost extent as permitted by rear block 129, which is affixed within vacuum spring tube 127 by any suitable method, and to a forwardmost extent as permitted by forward block 125, which is affixed within vacuum spring tube 127 by any suitable method.

In the example depicted, vacuum spring tube 127, forward block 125, and rearward block 129 form a partially enclosed cylinder and are substantially integral. Vacuum spring 139 resides in compression within vacuum spring tube 137, and is held at its forward end on vacuum spring boss 126 of forward block 125. The rearward end of vacuum spring 139 is held within vacuum spring retainer bore 137 within cutter block 136. Vacuum spring 139 is in compression between forward block 125 and moveable cutter block 136, and urges them away from each other. Thus, cutter 132 is urged rearward with respect to vacuum spring tube 127, and vice versa. Vacuum spring tube 127 may move longitudinally within body 105 as will be described further below.

In the example depicted, cutting spring 140 resides in compression within body 105, behind vacuum spring tube 127. The forward end of cutting spring 140 contacts and is constrained by the proximal end of vacuum spring tube 127 and/or rear block 129. The rearward end of cutting spring 140 contacts and is constrained by cutting spring retainer 141, which, in turn, rests against rear stop 106. Rear stop 106 is affixed within body and made integral therewith by screws or any other suitable method. Thus, cutting spring 140 urges vacuum spring tube 127 forward with respect to body 105. Cutting spring retainer 141 also has projecting therefrom cocking latch fingers 142 having beveled ends, which may flex inwardly toward each other as will be further described below.

Figure 18:
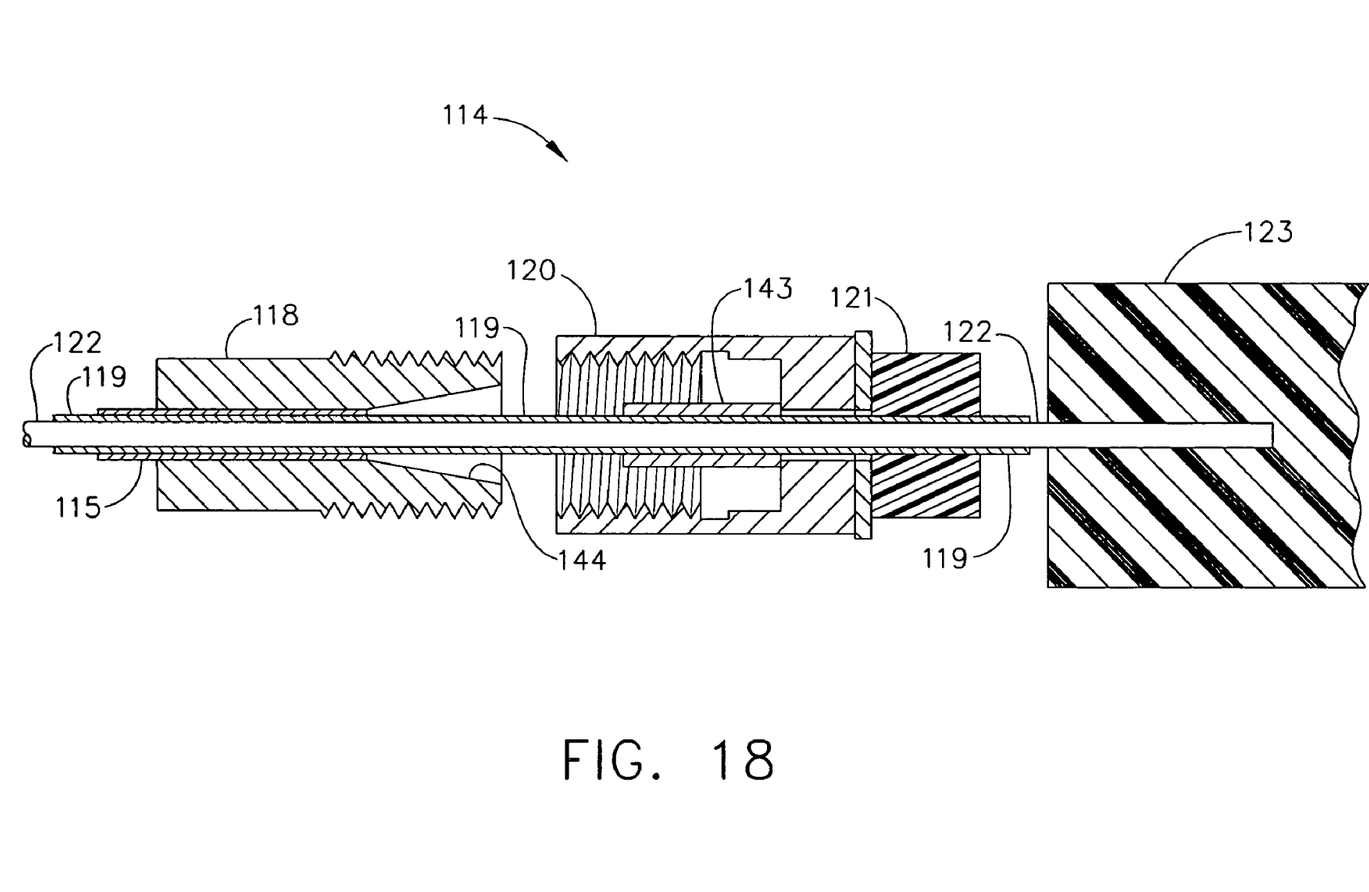
FIG. 18 is a longitudinal cross-sectional view of the rear components of an exemplary version of a plunger assembly.

Referring to FIGS. 1, 3, 5 and 18, one possible example of a suitable plunger is represented by plunger assembly 114, which includes retainer tube 15 having retainer tube end collar 116 integrally affixed to the distal end thereof by any suitable method and coupling hub 118 integrally affixed to the proximal end thereof by any suitable method. Within the exemplary device 100 in a pre-deployment position, retainer tube 115 with retainer tube end collar 116 extends forward to a point where retainer tube end collar 116 contacts a rear surface of cutter block 136 and/or cutter end collar 135 (see FIG. 5). Rearward longitudinal motion of retainer tube 119 is limited by contact of retainer tube end collar 116 with guide boss 150. One or more bumper rings 117 may be included on retainer rod 115 in the relative location shown in FIG. 3, to serve to dampen or absorb shock of collision between retainer tube end collar 116 and guide boss 150 when device 100 is actuated as will be described below. Coupling hub 118 has outside threads at its distal end as shown in FIG. 18, and has a tapered bore 144 in the distal end thereof.

In the example depicted, collection tube 119 is situated coaxially within retainer tube 115, and when device 100 is in a pre-deployment position, collection tube 119 extends forward within device 100 to a distal end proximate to the cutting tip 133 of cutter 132. Swivel hub 121 is integrally affixed by any suitable method to the proximal end of collection tube 119. Coupling knob 120 is rotatably affixed to swivel hub 121 and is rotatable about the longitudinal axis of, and relative to, collection tube 119. Coupling knob 120 has inside threads as shown, that mate with the outside threads of coupling hub 118. Coupling knob 120 also has a bushing 143 therein, about collection tube 119.

In the example depicted, plunger rod 122 resides coaxially within collection tube 119, and in a pre-deployment position extends forward within device 100 to a distal end proximate to the cutting tip 133 of cutter 132. Plunger mass 123 is integrally affixed to the proximal end of plunger rod 122 by any suitable method.

As noted, in the example depicted, plunger rod 122 is situated coaxially within collection tube 119, and collection tube 119 resides coaxially within retainer tube 115, and these three members may move longitudinally with respect to each other when not coupled together as will be described below. These three members may be sized so as to fit coaxially together substantially snugly, so that substantial quantities of air or other fluids may not pass through them for purposes of actuation of device 100 and effective development and maintenance of vacuum as will be described below. At the same time, their sizing may be selected so as not fit so snugly that substantially free relative longitudinal movement between them is prevented.

In the depicted example, with device 100 in the pre-deployment position shown in FIG. 5, the distally extending portions of collection tube 119 and plunger rod 22 extend distally out and forward from retainer tube end collar 116, into cutter end collar 135, and forward through cutter 132 such that the cutting tip 133 of cutter 132, the distal end of collection tube 119, and the distal end of plunger rod 122 are proximate to each other. Collection tube 119 may be sized so as to fit coaxially within cutter 132 substantially snugly, so that substantial quantities of air may not pass through them for purposes of actuation of device 100 and effective development and maintenance of vacuum as will be described below. At the same time, their sizing may be selected so as not to fit so snugly that substantially free relative longitudinal movement between them is prevented. Collection tube 119 may move longitudinally within cutter 132.

In the exemplary version of a plunger assembly 114 described and depicted, it will be appreciated that plunger rod 122, collection tube 119, and retainer tube 115 may be coupled together as follows. Referring to FIG. 18, when coupling knob 120 is brought into contact with coupling hub 118 and either or both are turned so that their respective mating threads engage and draw the respective members further together, bushing 143 about collection tube 119 is urged into tapered bore 144. As a result, bushing 143 is urged inwardly (towards the central longitudinal axis of the assembly), squeezing collection tube 119 inwardly against plunger rod 122. Thus, collection tube 119 grips plunger rod 122, and collection tube 119 and retainer tube 115 are coupled together by coupling of coupling hub 118 and coupling knob 120, and all of these members are coupled together so as to move together as a unit. It will be appreciated that coupling hub 118 and coupling knob 120 are only exemplary of a variety of coupling members that may be operably attached to components of a plunger assembly to effect coupling of a plunger rod, collection tube and retainer tube, and that other interacting and/or engaging coupling members may be used to effect such coupling. To facilitate gripping by collection tube 119 of plunger rod 122, but also provide for release and uncoupling of plunger assembly 114, it may be desirable that bushing 143 and collection tube 119 be formed of one or more suitable flexible and/or elastic materials such as plastic or other suitable materials that may be deformed and/or compressed relatively easily.

When retainer tube 115, collection tube 119 and plunger rod 122 of the exemplary version depicted are coupled together as described above, they still may move longitudinally within guide boss 150 of rear stop 106. Their forward longitudinal motion will be limited by contact of retainer tube end collar 116 with cutter end collar 135 and/or with cutter block 136, and their rearward longitudinal motion will be limited by contact of retainer tube end collar 116 with the forward end of guide boss 150. It will be appreciated that any other suitable cooperating features for limiting the longitudinal movement of a plunger or a plunger assembly to prevent premature or unwanted ejection or withdrawal from a device may be provided on a plunger or plunger assembly and associated housing, retaining, guiding or holding structures.

Operation of exemplary device 100 will now be described. As noted, FIGS. 1, 4 and 5 depict device 100 in its pre-deployment position. Cutter 132 and cutter tip 133 are in their most forward positions, proximate to the piercing tip 102 of probe 101, such that receiving aperture 103 is closed. Similarly, plunger assembly 114 is in its most distal position such that the distal ends of collection tube 119 and plunger rod 122 are proximate to cutting tip 133 of cutter 132, such that minimal air space exists within probe 101. Referring to FIG. 18 and the description above, retainer tube 115, collection tube 119 and plunger rod 122 have been coupled together via engagement of coupling knob 120 with coupling hub 118. With device 100 in this position, piercing tip 102 of probe 101 may be inserted through a patient's skin and into tissue, and probe 101 may be urged and guided by any suitable method through tissue toward a target tissue mass, until receiving aperture 103 is within or proximate to the target tissue mass. Alternatively, device 100 may be cocked first, prior to insertion of the probe into tissue.

Figure 2:
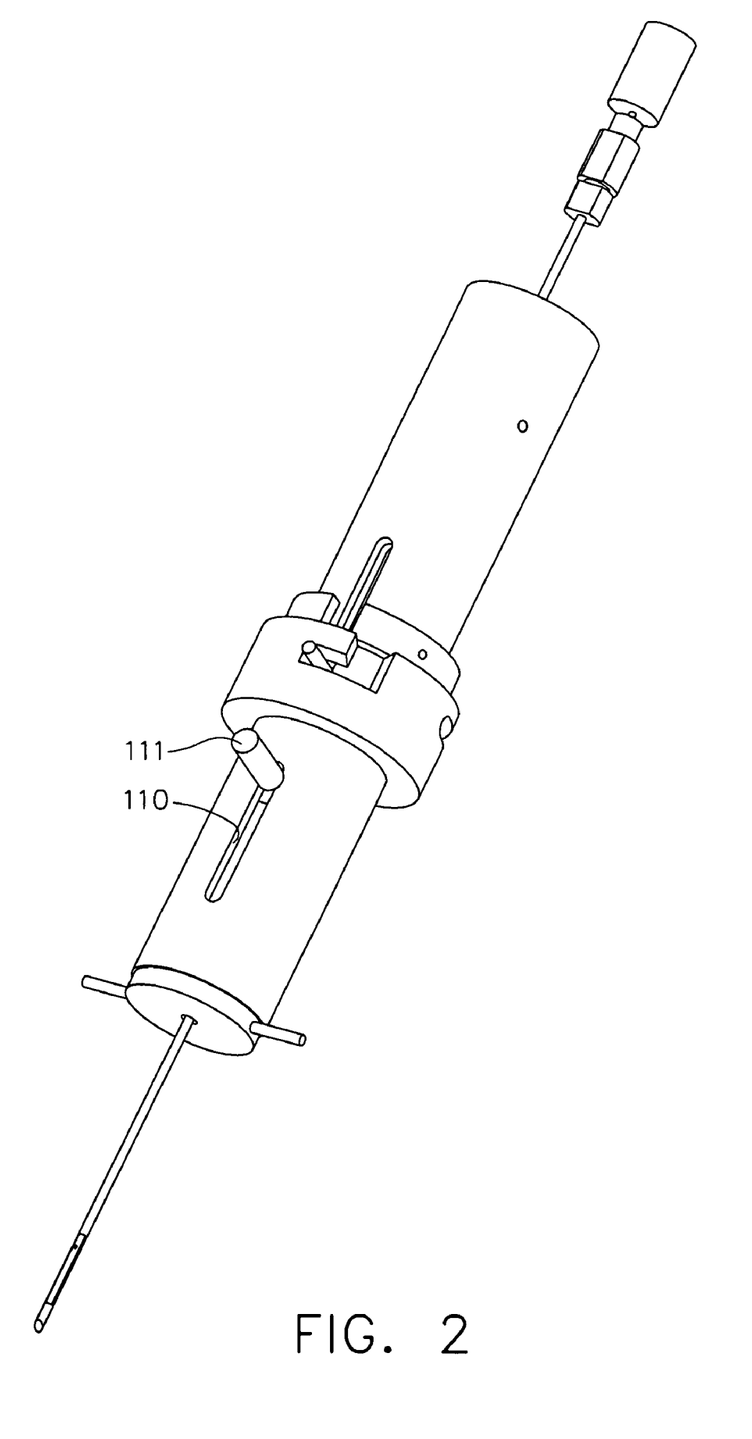
FIG. 2 is a perspective view of the device of FIG. 1, shown after it has been cocked and thereby made ready for actuation.
Figure 6:
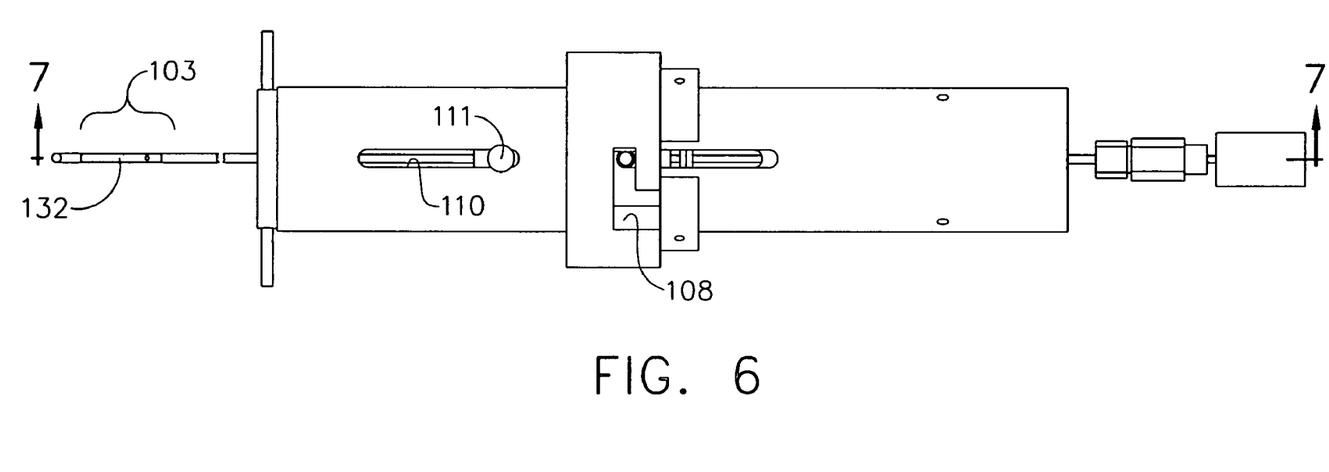
FIG. 6 is a side view of the device of FIG. 1, shown after it has been cocked and thereby made ready for actuation.
Figure 7:
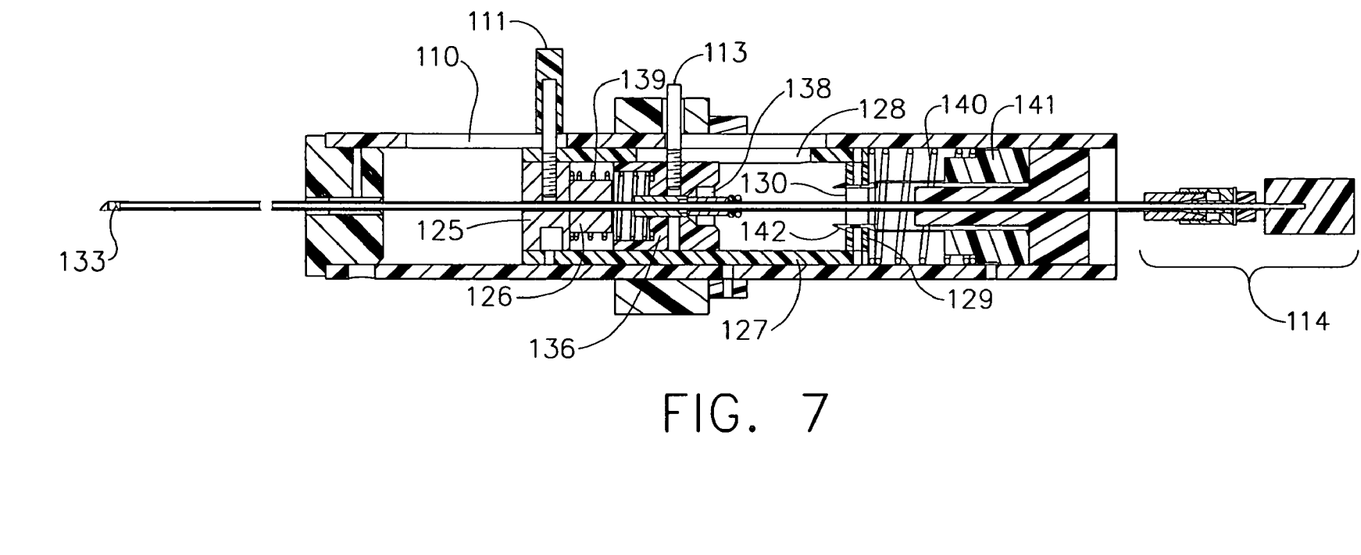
FIG. 7 is a longitudinal cross-sectional view of the device as shown in FIG. 6.

In order to cock exemplary device 100, the user may move cocking handle 111 rearwardly with respect to body 105, to the position shown in FIG. 2, and also FIGS. 6 and 7. It can be seen in FIG. 7 that the movement of cocking handle 111 effects corresponding longitudinal rearward movement of vacuum spring tube 127, to which cocking handle 111 is made integral via forward block 125. It can be seen that cutter block 136 has remained unmoved, in its starting position, held there by cutter latch pin 113 constrained in cutter latch 108 of cutter latch ring 107. As a result, vacuum spring 139 is longitudinally compressed between forward block 125 and cutter block 136. At the same time, cutting spring 140 is longitudinally compressed between the rearward end of vacuum spring tube 127 and/or rear block 129 integral therewith, and cutting spring retainer 141. Cocking latch fingers 142 extending from cutting spring retainer 141 have engaged through cocking catch bore 130 of rear block 129, and latched within it as shown in FIG. 7. Thus, it will be appreciated from FIG. 7 that when device 100 is cocked, vacuum spring 139 is compressed and ready to drive cutter block 136 rearward within vacuum spring tube 127, and cutting spring 140 is compressed and ready to drive vacuum spring tube 127 forward within body 105. However, because cutter block 136 has remained in its most forward, starting, position, cutter 132 and cutter tip 133 also have remained in their most forward, starting positions, proximate to the piercing tip 102 of probe 101, such that receiving aperture 103 remains closed. Similarly, plunger assembly 114 has remained in its most forward, starting, position such that the distal ends of collection tube 119 and plunger rod 122 remain proximate to cutting tip 133 of cutter 132, and such that minimal air space exists within probe 101. Referring to FIG. 18 and the description above, retainer tube 115, collection tube 119 and plunger rod 122 remain coupled together via engagement of coupling knob 120 with coupling hub 118. As shown in FIGS. 2, 6 and 7, device 100 is ready for actuation to draw tissue into the probe, sever and collect it.

Figure 8:
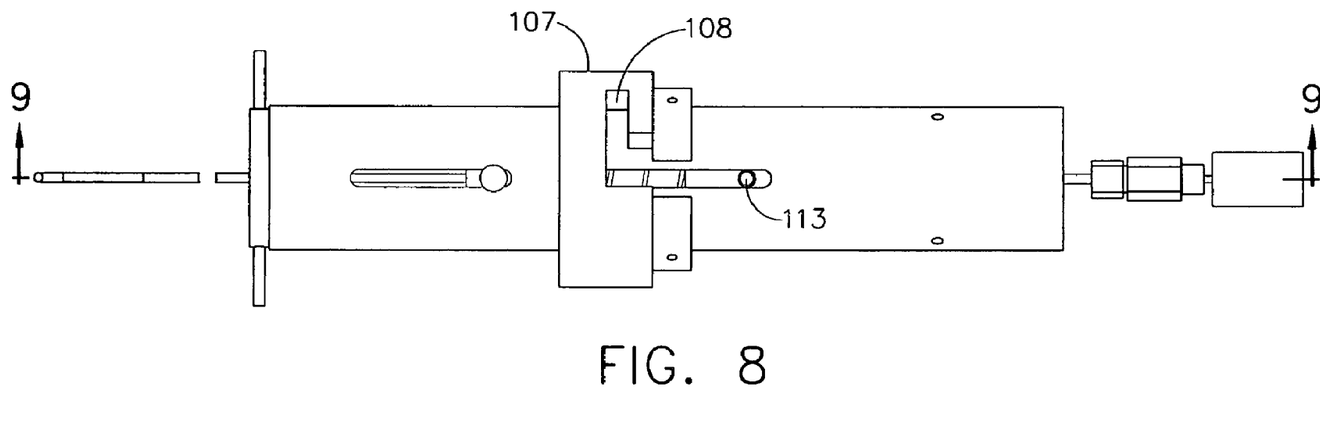
FIG. 8 is a side view of the device of FIG. 1, shown after it has been actuated and the cutter and plunger assembly have been driven rearward.
Figure 9:
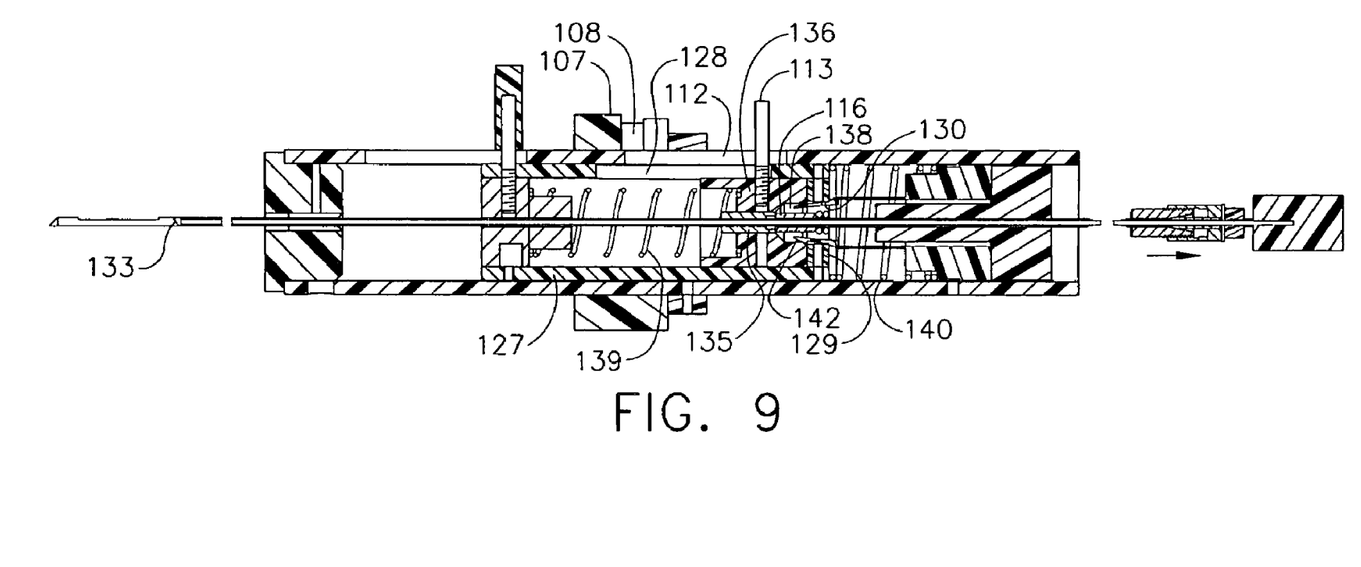
FIG. 9 is a longitudinal cross-sectional view of the device as shown in FIG. 8.
Figure 12:
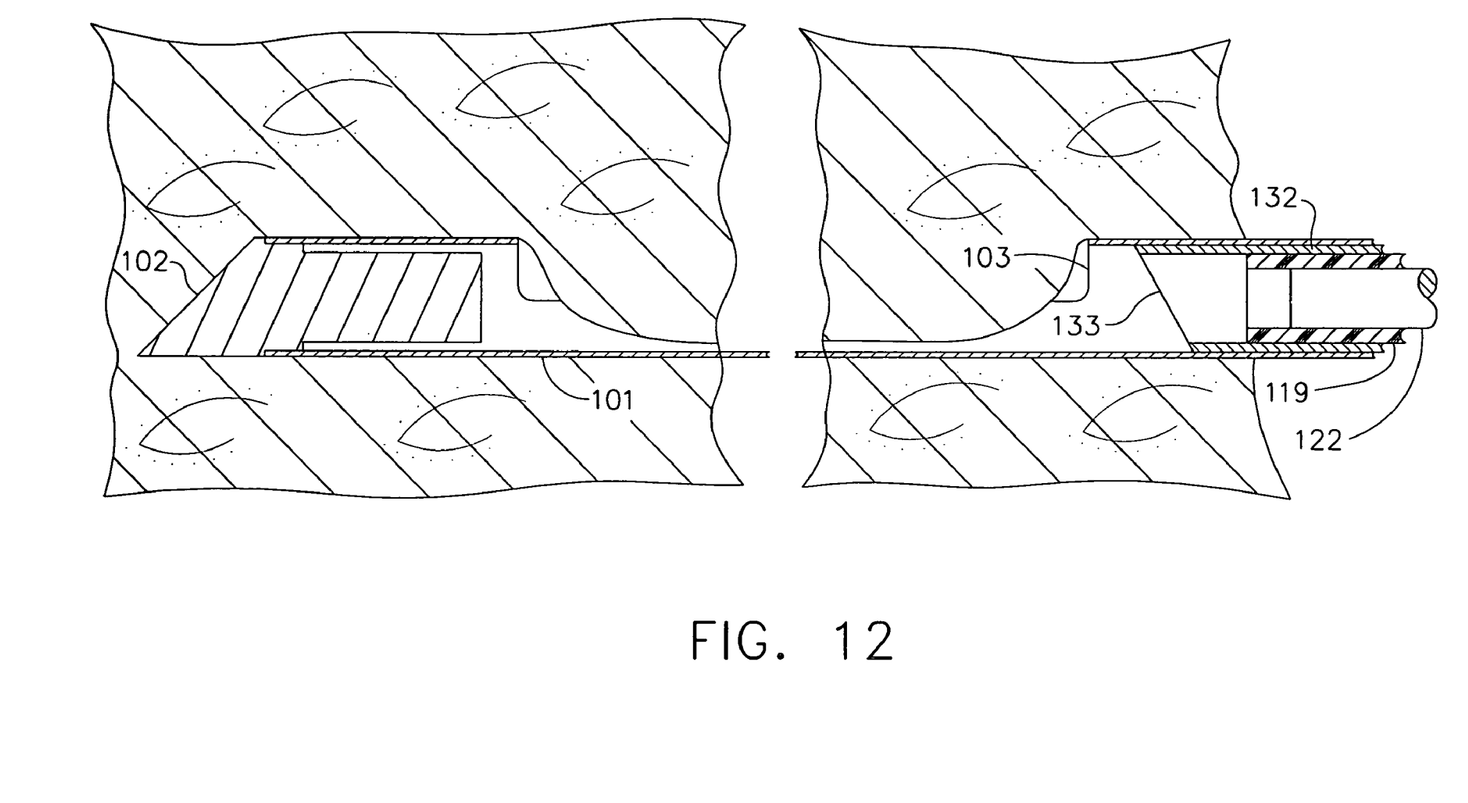
FIG. 12 is a longitudinal cross-sectional view of the probe end of the device of FIG. 1, shown inserted in tissue and illustrating positions of the cutter and plunger assembly just after the cutter has reversed direction.

In order to actuate exemplary device 100, the user may rotate cutter latch ring 107 about body 105, until cutter latch pin 113 is freed from cutter latch 108. FIGS. 8 and 9 depict a snapshot of device 100 following release of cutter latch pin 113, and correspondingly, following the rearward stroke of cutter block 136, but immediately prior to forward firing of cutter 132. Comparing FIG. 9 with FIG. 7 (showing device 100 in the cocked, pre-actuation position), it can be appreciated that with the release of cutter latch pin 113, cutter block 136 is driven rearward by vacuum spring 139. Rearward motion of cutter latch pin 113 is permitted by outer firing slot 112 in body 105 and by inner firing slot 128 in vacuum spring tube 127. When cutter block 136 is driven rearward, cutter 132 and plunger assembly 114 are also correspondingly driven rearward, by contact of cutter end collar 135 with retainer tube end collar 116. Referring to FIG. 12, it can be appreciated that when probe 101 is inserted within tissue to a depth such that receiving aperture 103 is completely within the tissue, the tissue will obstruct receiving aperture 103, preventing it from drawing in air. Thus, when cutter 132 and plunger assembly 114 all are driven rearward together, a vacuum will be created within the probe and at receiving aperture 103, drawing tissue thereinto. Referring again to FIG. 9, as cutter block 136 moves to its most rearward position within vacuum spring tube 127, the edges of cutter firing bore 138 within cutter block 136 contact the beveled ends of cocking latch fingers 142, urging them inward, just after vacuum has been created to draw tissue into the receiving aperture 103 as described above.

Figure 11:
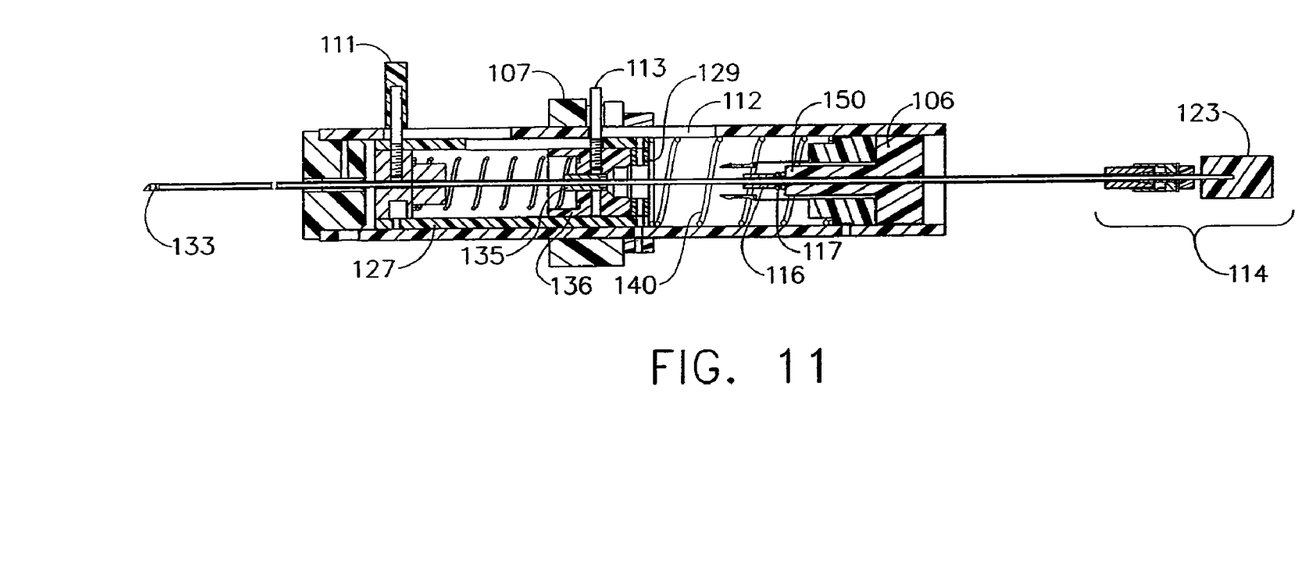
FIG. 11 is a longitudinal cross-sectional view of the device as shown in FIG. 10.
Figures 13, 14:
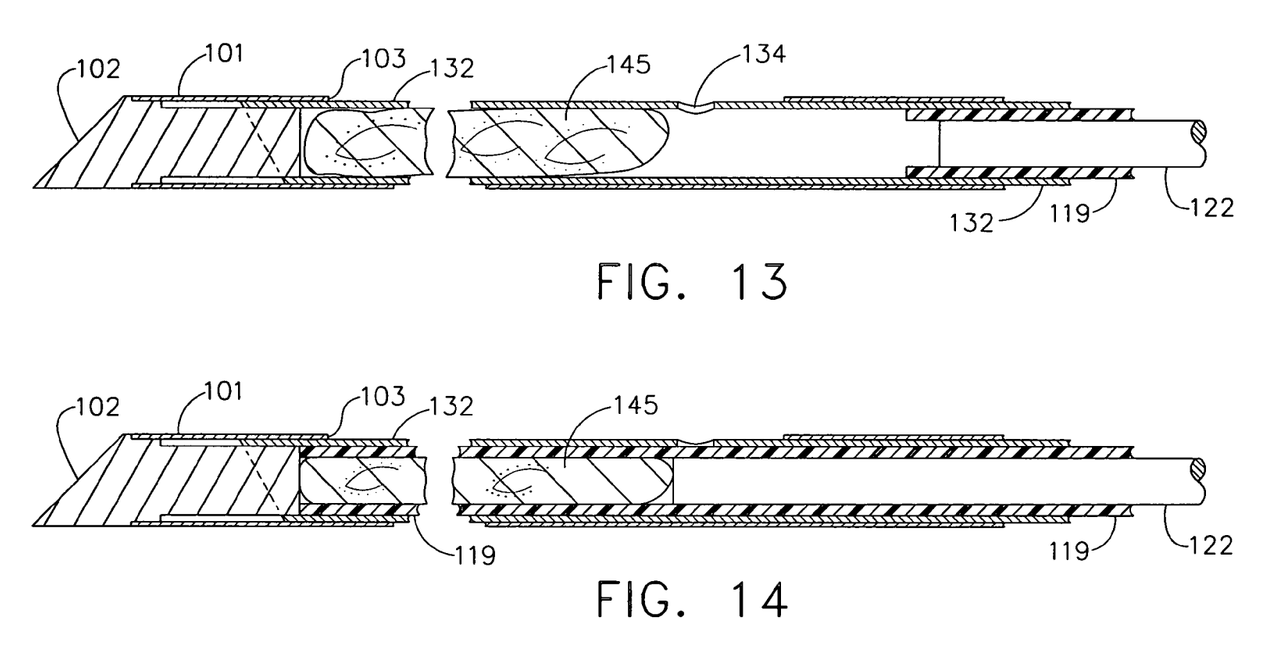
FIG. 13 is a longitudinal cross-sectional view of the probe end of the device of FIG. 1, shown after tissue has been severed and captured in the probe by the cutter, prior to advancement of the plunger assembly to collect the severed tissue.
FIG. 14 is a longitudinal cross-sectional view of the probe end of the device of FIG. 1, after the collection tube has been advanced to collect the severed tissue.
Figure 15:
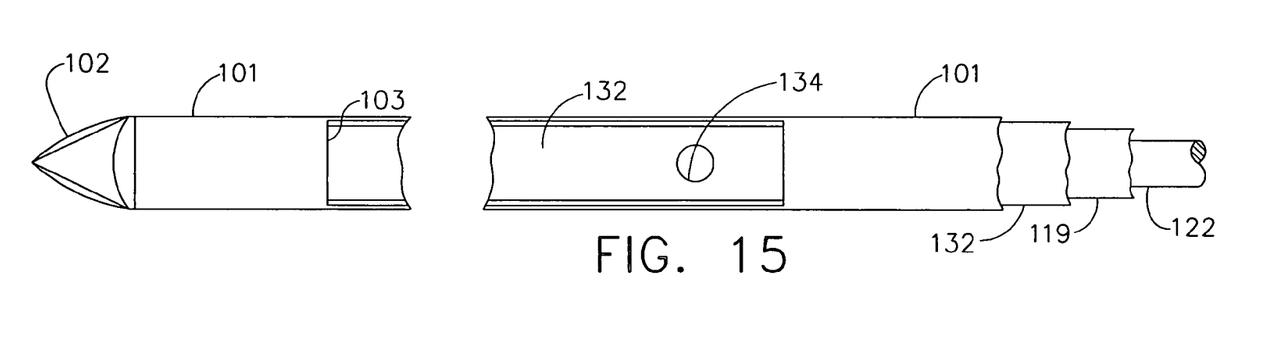
FIG. 15 is a partial perspective view of the probe end of the device of FIG. 1, illustrating the placement of a vent hole in the cutter as one possible mechanism for venting a probe.

In the exemplary version depicted, when the ends of cocking latch fingers 142 are urged inward, they unlatch and release their hold within cocking catch bore 130 in rear block 129, permitting vacuum spring tube 127 to be driven forward by cutting spring 140, acting upon the proximal end of vacuum spring tube 127 and/or rear block 129. The resulting forward stroke of vacuum spring tube 127 may be appreciated from a comparison of FIGS. 9 and 11. In FIG. 11, it can be seen that vacuum spring tube 127, and together with it, rear block 129, and thus cutter block 136 and cutter 132, have been driven forward by cutting spring 140. At the same time, the rearward momentum and kinetic energy in plunger assembly 114 developed during the rearward stroke previously described, which may be stored in part by plunger mass 123, keep collection tube 119 and plunger rod 122 of plunger assembly 114 moving rearward, maintaining vacuum at receiving aperture 103 in probe 101 and retaining tissue within the probe, to be severed as cutting tip 133 of cutter 132 advances forward past receiving aperture 103. It will be appreciated that an appropriate mass of an amount effective to preserve rearward momentum and movement of plunger assembly 114, during the reversal of direction and subsequent forward cutting stroke of cutter 132, can be imparted to and provided by coupling hub 118, coupling knob 120 and/or plunger mass 123, alone or in combination, and thus, any of these components alone or in combination may constitute an effective plunger mass. Rearward motion of plunger assembly 114 is checked by contact of retainer tube end collar 116 with guide boss 150 of rear stop 106. One or more bumper rings 117 may be included to dampen or absorb shock of the collision between retainer tube end collar 116 and guide boss 150. As cutter 132 advances forward, it severs tissue drawn into the probe, and captures it within itself. FIG. 13 depicts the distal end of probe 101 and the positions of the cutter 132, severed tissue 145, collection tube 119 and plunger rod 122 following the cutting stroke.

It will be appreciated from the description of the exemplary components and exemplary version set forth above that, following release of latch pin 113 effected by rotation of latch collar 107, the resulting rearward stroke of cutter 132 and plunger assembly 114, opening the receiving aperture 103 and simultaneously creating a vacuum that draws tissue into probe 101, followed by the forward stroke of cutter 132 to sever tissue, take place in coordinated, rapid sequence. Since creation of vacuum to draw tissue into receiving aperture 103 occurs with the rearward motion of cutter 132 and plunger assembly 114, it may be desirable that the device be configured such that the distal ends of collection tube 119 and plunger rod 122 be of a length sufficient to minimize the amount of air space within the probe when the device is in its pre-actuation position (e.g., FIG. 7), to minimize the amount of air present during actuation that will reduce the amount of vacuum developed within the probe 101 during the rearward stroke. It also will be appreciated that vacuum created by the rearward stroke is maintained by continued rearward motion of plunger assembly 114 under momentum developed during the rearward stroke, when the cutter's (132's) direction is reversed and it is driven forward in a cutting stroke.

Following the cutting stroke in the exemplary version depicted, cutter latch ring 107 may be rotated to its starting position (see, e.g., FIG. 4), recapturing cutter latch pin 113 in cutter latch 108. In this position, device 100 may be cocked again in preparation for another actuation while probe 101 is still in place in the tissue, to sever another tissue sample.

Before another actuation of the exemplary version depicted, the user may wish to either collect the previous sample severed, or adjust and reset plunger assembly 114 to maximize effectiveness. This may be accomplished in the exemplary version depicted by uncoupling plunger assembly 114. Referring to FIGS. 18, and also 13, 14 and 15, the user may first uncouple the exemplary plunger assembly 114 by unscrewing coupling knob 120 from coupling hub 118. This decouples retainer tube 115, collection tube 119 and plunger rod 122. Grasping coupling knob 120 and/or collection tube 119, and plunger mass 123 and/or plunger rod 122, the user may then advance collection tube 119, and along with it plunger rod 122, longitudinally within device 100. Referring to FIG. 13, as collection tube 119 and plunger rod 122 are advanced to the point where they contact the severed tissue, air or other fluid collecting within any space within cutter 132 may be vented out vent hole 134 as the plunger assembly is advanced within cutter 132, and will exit out along the tissue entry path of the probe. After plunger rod 122 has contacted the severed tissue, the user may stop advancing plunger rod 122, while continuing to advance collection tube 119 past and around the severed tissue to its most forward position, to capture the severed tissue therewithin. (See FIG. 14). Thereafter, the user may either withdraw collection tube 119 rearwardly entirely out of device 100 and eject the severed tissue from the collection tube by advancing plunger rod 122 therewithin, or alternatively, the user may re-couple retainer tube 115, collection tube 119 and plunger rod 122 by engaging coupling hub 118 and coupling knob 120 as described above.

Figure 17:
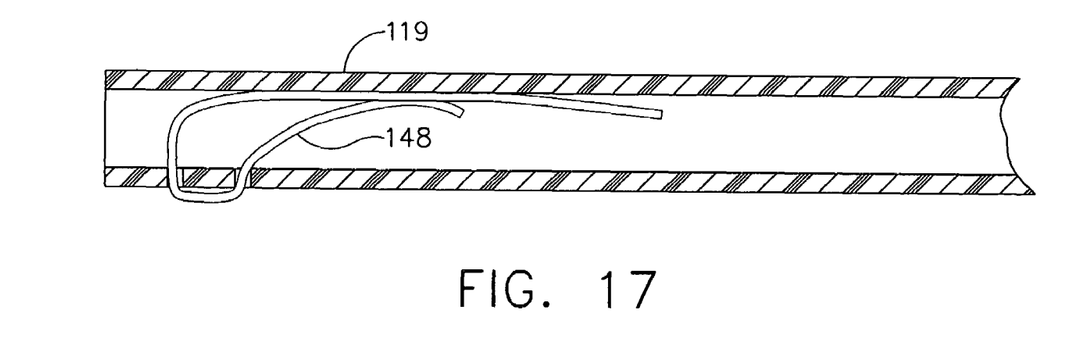
FIG. 17 is a longitudinal cross-sectional view of the distal end of a version of a collection tube having one possible mechanism for retaining severed tissues therein.

FIG. 17 depicts one possible version of a mechanism for retaining severed tissue within a collection tube such as collection tube 119. This may be desirable, for example, when multiple samples are to be severed and collected in collection tube 119 before they are removed from device 100, to prevent their inadvertent ejection from collection tube 119 as device 100 is being used. Two holes are formed proximate the distal end of collection tube 119, and a suitably formed retainer wire 148, such as, for example, 0.004" diameter NITINOL wire, is inserted therethrough, with ends protruding rearwardly into the collection tube lumen as shown. As tissue enters the distal end of collection tube 119 and passes the ends of retainer wire 148, the ends will catch in the tissue should it be urged forward, thereby preventing it from exiting the distal end of the collection tube 119. When it is desired to eject the severed tissue from the distal end of collection tube 119, using for example, plunger rod 122, retainer wire 148 may be removed, to permit the tissue to exit collection tube 119. Other alternative retaining devices or structures may be provided proximate to the end of collection tube 119, including devices or structures having rearwardly projecting barbs or other tissue-catching structures.

Figure 16:
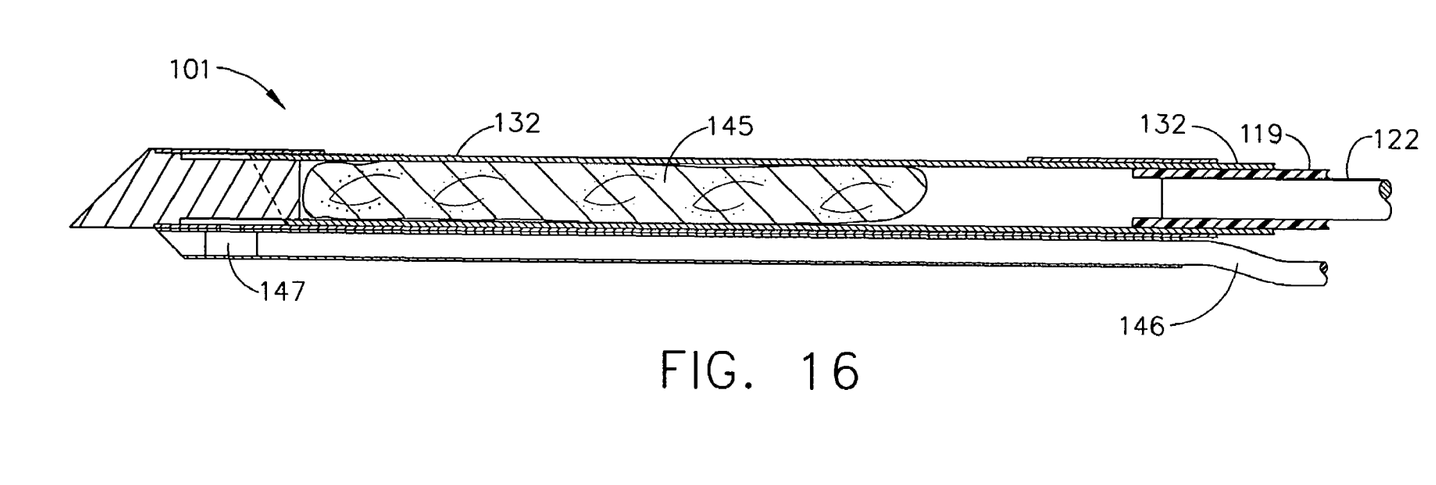
FIG. 16 is a longitudinal cross-sectional view of an alternative version of a probe end, illustrating one alternative mechanism for venting a probe.

As shown in FIG. 16, a probe 101 may include a separate tube or other structure creating vent lumen 147 that allows air to move into probe 101 as the plunger assembly is being withdrawn, for example, to remove tissue samples that have been collected. This can help to prevent vacuum, created by withdrawal of the plunger assembly, from pulling tissue samples from the collection tube as it is being withdrawn. Such a separate vent lumen as, for example, vent lumen 147, also can serve to vent air from probe 101 as a plunger such as plunger assembly 114 is being reinserted in preparation for severing another tissue sample. Following reinsertion of the plunger, vent lumen 147 may be plugged with, for example, vent plug 146. Additionally, a vent lumen such as vent lumen 147 may substitute for, or supplement, the venting function provided by a vent hole 134 in cutter 132.

In the exemplary version depicted, after collection tube 119 has been advanced to capture severed tissue 145, and after plunger rod 122 has been advanced into contact with severed tissue 145, or alternatively, after severed tissue 145 has been removed from collection tube 119 and plunger assembly 114 reinserted into device 100, plunger assembly 114 may be coupled together again as described above, and device 100 may be cocked, in preparation for another actuation to sever and capture an additional tissue sample. It will be appreciated from the foregoing description that multiple tissue samples may be collected using the exemplary version described, while probe 101 remains in place within the tissue.

It also will be appreciated that the exemplary components and versions of a device 100 described herein create and utilize vacuum to draw tissue into a receiving aperture of a probe 101, and that the vacuum is provided by mechanisms within device 100 itself, without the necessity for connection to an outboard vacuum source. Similarly, it will be appreciated that the described versions do not require any external source of power for operation because mechanisms within device 100 include driving mechanisms, for example, vacuum spring 139 and associated components, and cutting spring 140 and associated components.

Vacuum to draw tissue into the exemplary probe 101 is provided in the exemplary device 100 substantially by the rearward motion of a plunger such as plunger assembly 114 that fits effectively snugly within cutter tube 132. Depending upon the particular configuration of the device, it may be desirable to have cutter 132 to fit effectively snugly within probe 101, or to provide another suitable configuration to ensure the development and maintenance of sufficient vacuum within probe 101 prior to the severing of the tissue sample. It will be appreciated also that the required vacuum may be provided in the alternative by the motion of one or more members or alternative plunger assemblies, such as a single plunger or plunger rod, fitting effectively snugly and longitudinally movable within a hollow longitudinal member in fluid communication with a receiving aperture, such as receiving aperture 103 on probe 101.

In the exemplary components and versions described herein, the driving force to effect rearward motion of the plunger assembly 114 is supplied by a compressed spring, vacuum spring 139. However, it will be appreciated that such driving force can be supplied by any other suitable driving mechanism, such as but not limited to other types of springs in compression, tension, flexion or torsion, by other longitudinally motive devices such as gas or fluid cylinders or levers and/or gear-driven devices operably configured to store and release potential energy to supply longitudinal motive forces, or alternatively, to supply longitudinal motive forces by converting and/or transferring forces developed or supplied through other mechanisms. For example, suitable longitudinal forces might by supplied by hand-operated or motor-driven lever and/or gear mechanisms, used in conjunction with one or more spring devices, or not. It will be appreciated that if a plunger takes the form of a rod or other member extending from a distal end within a probe to a proximal portion protruding from a proximal portion of a device, the force necessary to retract the plunger rearwardly and thereby create a vacuum within the probe may be supplied by hand (by pulling rearwardly on the plunger) or a hand-operated mechanism.

Similarly, in the exemplary components and versions described herein, the forces to effect sequential rearward (receiving aperture 103 opening) motion of the cutter 132, and then forward (cutting) motion of the cutter 132, are also supplied by compressed coil springs, vacuum spring 139 and cutting spring 140. However, it will be appreciated that such forces can be supplied by any other suitable driving mechanisms, such as but not limited to other types of springs in compression, tension, flexion or torsion, by other longitudinally motive devices such as gas or fluid cylinders or levers and/or gear-driven devices operably configured to store and release potential energy to supply longitudinal motive forces, or alternatively, to supply longitudinal motive forces by converting and/or transferring forces supplied through other mechanisms. For example, suitable longitudinal forces might by supplied by hand-operated or motor driven lever and/or gear mechanisms, used in conjunction with one or more spring devices, or not.

It will be apparent that the vacuum supplied by a plunger such as plunger assembly 114, that draws tissue into receiving aperture 103 in the exemplary versions depicted, is supplied during or after opening of the receiving aperture 103 and before or during a cutting stroke. It will be appreciated that such vacuum may be supplied effectively while a receiving aperture is open, and effectively prior to and during at least a portion of the time a cutting edge moves across such receiving aperture in a cutting stroke, so as to provide that tissue is drawn into and present within a probe so that it can be severed in a cutting stroke. It will be understood, however, that simultaneous movement of a cutter and a plunger prior to a cutting stroke may be desirable in some circumstances for purposes of configuration of the driving mechanism(s) or other structures, but is not necessarily required to effect the proper timing of creation of vacuum within the probe. Accordingly, the respective motions of a plunger and a cutter may be decoupled and effected by separate mechanisms to provide for the creation of vacuum that is suitably timed with respect to a cutting stroke to ensure that tissue is drawn into a probe and situated in a position in which it can be effectively severed and removed by an associated device.

Thus, another version of a cutter (not shown) may be configured to cut during a rearward motion, instead of a forward motion, and an appropriate effectuating mechanism configured. For example, an alternative hollow cutter (not shown) may be provided that is situated and moves within, or outside and along, a probe, with such alternative cutter having therein a window that is effectively longitudinally aligned with, and travels rearwardly past, a receiving aperture on such a probe, with the distal edge of the window being suitably formed and sharpened to form a cutting edge that travels past such receiving aperture in a rearward direction. In this version, the window in such alternative cutter may be placed so that when such alternative cutter is fully advanced, the window is beyond, or distal to, the receiving aperture, thereby closing the receiving aperture. As this version of an alternative cutter is drawn rearward, the window will move across the receiving aperture, opening it, and with continuing rearward motion the cutting edge on the distal edge of the window will move across the receiving aperture in a rearward direction. It can be appreciated that a suitable mechanism can be configured to move a plunger within a hollow longitudinal member, in fluid communication with the receiving aperture, in unison and/or in coordination with such rearward motion of such alternative cutter, thereby providing that vacuum is effectively provided within the probe when the receiving aperture is opened and before or during the rearward movement of the cutting edge across the receiving aperture.

Figure 10:
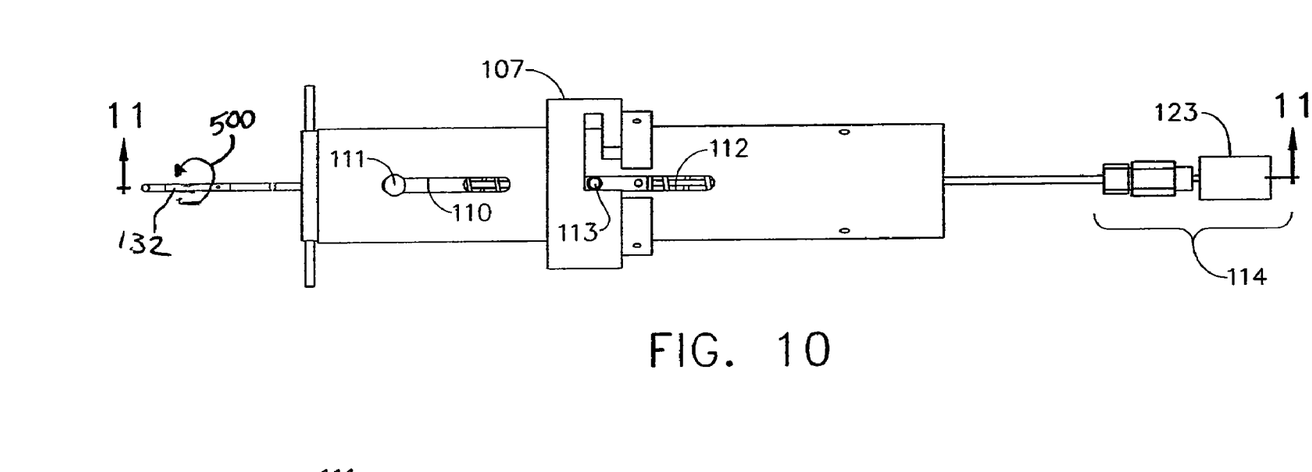
FIG. 10 is a side view of the device of FIG. 1, shown after the cutter has been driven forward.

In another possible version, an alternative rotating cutter and associated drive mechanism (not shown) can be designed wherein rotation of this alternative rotating cutter about or within a probe will open a receiving aperture in the probe, and then pass a cutting edge across it, via rotation of such a rotating cutter. The rotatability of the cutter is illustrated by the arrow 500 shown in FIG. 10. Again, it can be appreciated that a mechanism can be configured to move a plunger within a hollow longitudinal member that is in fluid communication with the receiving aperture, in coordination with rotation of such rotating cutter, thereby providing that vacuum is effectively provided within the probe when the receiving aperture is opened, and before or during the movement of the cutting edge across the receiving aperture.

From the foregoing, it will be appreciated that a cutter can take a variety of forms having a cutting edge situated to be moved across the receiving aperture of a probe in any suitable motion, driven by any suitable mechanism. Similarly, a mechanism by which a receiving aperture is opened and closed may be combined with, or separate from, a cutter or a mechanism that moves a cutter.

The exemplary versions described and depicted herein involve trip mechanisms (for example, the interacting combination of cutter latch ring 107 and cutter latch pin 113, and the interacting combination of cocking latch fingers 142, cocking catch bore 130 of rear block 129, and cutter firing bore 138 of cutter block 136) for alternately restraining, and then releasing, members upon which springs exert force, to effect driving of the components. It will be appreciated that if springs or other devices having therein stored potential energy are used to supply motive forces, suitable trip mechanisms to alternately restrain and then release such devices may take a variety of suitable forms in addition to the examples described and depicted herein.

Tubes or cylinders having integral end blocks or stops are depicted in the described exemplary versions, for housing or holding the mechanisms described, for example, body 105 with forward stop 104 and rear stop 106, and vacuum spring tube 127 with forward block 125 and rear block 129. It will be appreciated, however, that other shapes and forms of housings may be used. For example, a body may be provided with suitable handle features or other ergonomic features to enhance appearance, utility, effectiveness and/or convenience. Similarly, a body may be provided with suitable mounting features if the associated device is to be used in conjunction with insertion-guiding, holding and/or immobilizing devices or fixtures. With respect to internal components such as, for example, vacuum spring tube 127, any suitable housings or structures may be employed to operably house or hold mechanisms to effect the respective coordinated motion of a cutter and longitudinal motion of a plunger and/or plunger assembly within a probe, to provide coordinated application of vacuum to draw in tissues, and a subsequent cutting stroke.

It also will be appreciated that the exemplary version of the probe 101 and plunger assembly 114 configuration described herein may be altered while still providing vacuum to draw in tissues, created by a plunger moving within a hollow longitudinal body in fluid communication with a receiving aperture in a probe. For example, a moving cutter may be located outside, rather then inside, of a probe. A plunger may be located and movable within a longitudinal hollow member in fluid communication with a receiving aperture, and such hollow member may comprise a hollow cutter, a hollow probe, a collection tube or a separate hollow member that is fluidly connected to the receiving aperture in the probe, to create vacuum to draw tissue into the receiving aperture. A probe may have a distal piercing tip, or an incising tip, if it is desired to have a probe create its own path of insertion into the tissues. Alternatively, another instrument might first be used to create a path of insertion into the tissues, and a probe might have a rounded or other suitably shaped tip to facilitate insertion along the path.

Having shown and described various versions and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings.

VACUUM PLUNGER CORE NEEDLE -
PARTS REFERENCE LIST 100 device
101 probe
102 piercing tip -continued

VACUUM PLUNGER CORE NEEDLE -
PARTS REFERENCE LIST 103 receiving aperture
104 forward stop
105 body
106 rear stop
　　150 guide boss
107 cutter latch ring
　　149 rotation slot
108 cutter latch
109 shoulder ring
110 cocking slot
111 cocking handle
112 outer firing slot
113 cutter latch pin
114 plunger assembly
115 retainer tube
116 retainer tube end collar
117 bumper rings
118 coupling hub
　　144 tapered bore
119 collection tube
120 coupling knob
　　143 bushing
121 swivel hub
122 plunger rod
123 plunger mass
124 cocking assembly
125 forward block
126 vacuum spring boss
127 vacuum spring tube
128 inner firing slot
129 rear block
130 cocking catch bore
131 cutter assembly
132 cutter
133 distal cutting tip
134 vent hole
135 cutter end collar
136 cutter block
137 vacuum spring retainer bore
138 cutter firing shoulder
139 vacuum spring
140 cutting spring
141 cutting spring retainer
142 cocking latch finger(s)
143 bushing
144 tapered bore
145 severed tissue
146 vent plug
147 vent lumen
148 retainer wire
149 rotation slot
150 guide boss

We claim:

1. device for severing and removing internal tissues, comprising:
　a body;
　a hollow probe affixed to said body, said probe having a receiving aperture thereon and a free distal end;
　a cutter having a hollow distal portion within said probe and a cutting edge on said distal portion, said cutter being longitudinally movable between a first position and a second position within said probe, wherein said cutter is operable to at least partially obstruct said receiving aperture when said cutter is in said first position;
　a plunger having a distal portion within said cutter, and longitudinally movable within said cutter;
　a first spring held by said body and in mechanical communication with said cutter and said plunger;
　a second spring held by said body and in mechanical communication with said cutter;

a first trip mechanism held by said body, wherein said first trip mechanism is operable to alternately effect restraint of said first spring when said first spring is loaded, and effect release of said first spring; and a second trip mechanism held by said body, wherein said second trip mechanism is operable to alternately effect restraint of said second spring when said second spring is loaded, and effect release of said second spring;

wherein the cutter is operable to remain stationary in said first position when said first spring and said second spring are loaded;

wherein release of said first spring causes said cutter to travel proximally within said probe toward said second position, thereby opening said receiving aperture, wherein release of said first spring further causes tripping of said second trip mechanism to effect release of said second spring, wherein release of said second spring causes said cutter to travel distally within said probe toward the first position.

2. The device of claim 1 wherein said plunger further comprises a first tube and a rod coaxially within said first tube.

3. The device of claim 2 wherein said plunger further comprises a second tube coaxially outside said first tube.

4. The device of claim 2 further comprising a coupling member attached to said plunger, and operable to selectively couple and decouple said first tube to said rod.

5. The device of claim 3 further comprising a first coupling member attached to said plunger and a second coupling member attached to said plunger, and wherein said first and said second coupling members are operable to selectively engage and disengage with each other and thereby selectively couple and decouple said first tube, said second tube and said rod together.

6. The device of claim 1 further comprising a mass attached to said plunger.

7. The device of claim 2 further comprising a mass attached to said plunger.

8. A device for severing and removing internal tissues, comprising:
   a body;
   a hollow probe affixed to said body, said probe having a receiving aperture thereon and a free distal end;
   a cutter having a cutting edge thereon, said cutting edge being proximate to said receiving aperture and said cutter being movable with respect to said receiving aperture such that said cutting edge moves across said receiving aperture;
   a plunger having a distal portion within said probe, and longitudinally movable within said probe; and
   a cutter driving mechanism held by said body and in mechanical communication with said cutter, wherein said cutter driving mechanism drives said cutter so that said cutting edge moves across said receiving aperture, wherein said cutter driving mechanism comprises a first spring that drives said cutter longitudinally with respect to said probe in a proximal direction upon release of said first spring, wherein said cutter driving mechanism further comprises a second spring that drives said cutter longitudinally with respect to said probe in a distal direction upon release of said second spring.

9. The device of claim 8 wherein said cutter further comprises a distal portion, and wherein said cutting edge is proximate to said distal portion, and said cutter is longitudinally movable with respect to said probe.

10. The device of claim 8 wherein said cutter is outside of said probe.

11. The device of claim 8 wherein said cutter rotates with respect to said probe.

12. The device of claim 8 wherein said first spring drives said plunger longitudinally within said probe.

13. The device of claim 8 wherein said plunger further comprises a tube and a rod coaxially within said tube.

14. The device of claim 8 further comprising a mass attached to said plunger.

15. The device of claim 13 further comprising a mass attached to said plunger.

16. A device for severing and removing internal tissues, comprising:
   a body;
   a hollow probe affixed to said body, said probe having a receiving aperture thereon and a free distal end;
   a plunger having a distal portion within said probe, and longitudinally movable within said probe;
   a plunger driving mechanism held by said body and in mechanical communication with said plunger, wherein said plunger driving mechanism comprises at least one spring in mechanical communication with said plunger;
   a cocking mechanism in mechanical communication with the plunger driving mechanism, wherein the cocking mechanism is configured to transition said at least one spring from a relaxed state to a loaded state; and
   an actuation mechanism, wherein the actuation mechanism comprises a latch ring and a latch pin, wherein said latch ring comprises an annular member with a retaining slot, wherein said latch pin is in communication with said at least one spring, wherein said at least one spring urges said latch pin in a proximal direction once said at least one spring is in said loaded state; wherein said latch ring is configured to rotate between a first position and a second position, wherein said latch ring is configured to retain said latch pin within said retaining slot thereby preventing said latch pin from traveling in a proximal direction while in said first position, wherein said latch ring is configured to release said latch pin from said retaining slot thereby allowing said latch pin to travel in a proximal direction while in said second position;
   wherein said plunger driving mechanism drives said plunger longitudinally within said probe in response to said at least one spring transitioning from said loaded state toward said relaxed state, and wherein longitudinal movement of said plunger within said probe away from said receiving aperture creates a vacuum within said probe when said receiving aperture is obstructed.

17. The device of claim 16, wherein said plunger further comprises:
   a tube;
   a rod coaxially within said tube; and
   a coupling member attached to said plunger, wherein said coupling member is configured to selectively effect coupling and decoupling of said rod to said tube.

18. The device of claim 16 further comprising a mass attached to said plunger.

19. The device of claim 16 further comprising:
   a cutter having a cutting edge thereon, said cutting edge being proximate to said receiving aperture and said cutler being movable with respect to said receiving aperture such that said cutting edge moves across said receiving aperture; and
   a cutter driving mechanism held by said body and in mechanical communication with said cutter, wherein said cutter driving mechanism drives said cutter so that said cutting edge moves across said receiving aperture.

* * * * *